United States Patent [19]

Yamauchi et al.

[11] 4,259,117
[45] Mar. 31, 1981

[54] DENTAL FILLING MATERIAL

[75] Inventors: Junichi Yamauchi, Kurashiki; Eiichi Masuhara, Bunkyo-Ward; Nobuo Nakabayashi, Matsudo; Kyoichiro Shibatani, Kurashiki; Tooru Wada, Takatsuki, all of Japan

[73] Assignee: Kuraray Co., Ltd., Okayama, Japan

[21] Appl. No.: 936,759

[22] Filed: Aug. 25, 1978

Related U.S. Application Data

[63] Continuation of Ser. No. 778,734, Mar. 17, 1977, abandoned.

[30] Foreign Application Priority Data

Mar. 17, 1976 [JP] Japan ................................. 51/30045
Nov. 29, 1976 [JP] Japan ............................... 51/143807
Nov. 30, 1976 [JP] Japan ............................... 51/145049

[51] Int. Cl.$^3$ .............................................. C09K 3/00
[52] U.S. Cl. ........................................ 106/35; 260/42; 260/998.11; 433/217; 433/228; 526/277; 526/278
[58] Field of Search ..................... 106/35; 260/998.11, 260/42; 526/277, 278; 433/217, 228

[56] References Cited

U.S. PATENT DOCUMENTS

| | | | |
|---|---|---|---|
| 3,346,545 | 10/1967 | Sehm | 526/277 |
| 3,754,972 | 8/1973 | de Majistre et al. | 260/928 |
| 3,884,864 | 5/1975 | Matsuda et al. | 526/277 |
| 3,987,127 | 10/1976 | Dickie et al. | 204/159.15 |
| 4,001,150 | 1/1977 | Juna et al. | 526/277 |
| 4,044,044 | 8/1977 | Saito | 526/277 |

FOREIGN PATENT DOCUMENTS 947471 of 0000 United Kingdom .
982577 2/1965 United Kingdom .
1090249 11/1967 United Kingdom .
1374633 11/1974 United Kingdom .

Primary Examiner—Lorenzo B. Hayes
Attorney, Agent, or Firm—Oblon, Fisher, Spivak, McClelland & Maier

[57] ABSTRACT

A dental filling agent is provided, which contains a phosphoric or phosphonic acid ester compound containing at least one polymerizable functional group and either a group of the formula

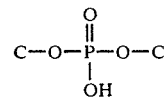

or a group of the formula

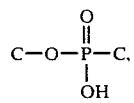

or a high molecular weight compound obtainable by polymerizing the compound either alone or as a comonomer unit. This agent has a high bonding affinity for the tooth and enjoys prolonged stability in wet environments.

10 Claims, No Drawings

DENTAL FILLING MATERIAL

This is a continuation, of application Ser. No. 778,734, filed Mar. 17, 1977, now abandoned.

BACKGROUND OF THE INVENTION

1. Field of the Invention

This invention relates to adhesive cementing agents for the hard tissues of the human body, including teeth and bones. More particularly, the invention relates to adhesive cementing agents of the type in which an intimate bonding affinity for human tissues is desired, such as cements for the treatment of a complex fracture of bone or for fixation of artificial joints, dental adhesives, dental fillers, dental restorative, and so forth.

2. Description of the Prior Art

In the conventional dental filling agents of the cold-cure type (curable at room temperature) as well as the cementing agents for the fixation of artificial joints, a mixture of polymethyl methacrylate and methyl methacrylate or a mixture of bisphenol-A diglycidyl dimethacrylate and triethylene glycol dimethacrylate, among other combinations, are employed and allowed to cure in situ in the presence or absence of an inorganic filler, mainly by means of a peroxide-amine catalyst system which generates free radicals. The cured composition obtainable by this known method has substantially no bonding affinity for human tissues (except for acid treated dental enamel), the bonding strength under wet conditions being as low as about 0 to 5 kg/cm². For this reason, in the conventional filling practice, e.g. for the treatment of caries, mechanical retainer means known as undercuts have been applied to the cavity to lock the cured filling agent in position. This procedure, however, is disadvantageous in that it removes the healthy portion of the tooth and in that because of the lack of bond between the filler and the tooth proper, it provides only a poor marginal seal which often permits a relapse of tooth decay or other tissue defect. As a preventive filling agent and an orthodontial cement, both adapted to provide a sealing bond with the tooth, adhesive agents based on α-cyanoacrylate have been developed in recent years, but these agents are known to lack durability in the oral cavity as well as in have poor handleability. A dental cement-filling agent containing a trialkylboron compound as a polymerization initiator ingredient has also been developed (Japanese Patent Publication No. 14318/1967 and No. 29195/1970), but while it provides a firm bond with the dentin, it does not have adequate bonding affinity for the enamel. Moreover, since the resin employed is primarily based on methyl methacrylate, this product is not fully satisfactory for dental filling purposes. A procedure has also been developed which employs a vinyl compound containing a divalent phosphoric acid

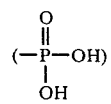

group which is claimed to provide a bond with the calcium of the tooth (Japanese Patent Application laid-open No. 44152/1976; Journal of Dental Research 35, 846). However, its low adhesive strength does not make the product sufficiently useful for most practical purposes. U.S. Pat. No. 3882600 discloses that the addition of a small amount of an addition-polymerizable phosphoryl monofluoride to a dental cement composition results in an improved bond between the tooth and the composition. However, this product seems to be not truly safe to the pulp because of its interaction with the tooth which is conceivably due to the P-F bond contained in the product.

SUMMARY OF THE INVENTION

It is, therefore, an object of this invention to provide a cement for the hard tissues of the human body which has adequate hardness, compressive strength and other mechanical properties, as well as water absorption characteristics, affords a firm and lasting bond with the hard tissue of the human body, including bones and the dentin and enamel of tooth and is nontoxic to human beings.

It is another object of this invention to provide a clinically useful cement for application to the hard tissue of the human body which is especially of value as a filling composition for the tooth.

It is still another object of this invention to provide an adhesive agent for the hard tissue of the human body which is of value as an adhesive agent for binding a dental filler to the tooth or which is useful as a filling material for teeth.

Other objects of the invention will be apparent from the following detailed description.

These objects are accomplished by the adhesive cementing agent of this invention which contains a phosphoric or phosphonic acid ester compound containing at least one polymerizable functional group and at least one

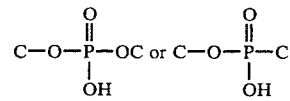

bond, or a high molecular weight compound obtainable by polymerizing said phosphoric or phosphonic acid compound either alone or with another compound.

DETAILED DESCRIPTION OF THE PREFERRED EMBODIMENTS

The phosphoric or phosphonic acid ester compound containing at least one polymerizable functional group and a linkage of the formula

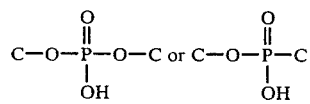

is preferably a compound containing at least one

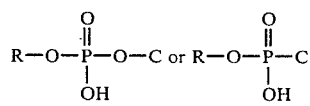

bond, (wherein R is an organic residue containing at least one polymerizable functional group. More particularly, the compound is preferably one of the compounds represented by the following formulas (1) to (7).

(A) Thus, the compound may be a compound represented by the general formula:

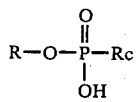

(1)

wherein R is an organic residue containing at least one polymerizable functional group; Rc means X or OX where X is either a straight-chain, cyclic or branched aliphatic, alicyclic or aromatic hydrocarbon residue containing 1 to 30 carbon atoms, which residue may optionally be substituted by hydroxyl, halogen, amino or carboxyl group, or X is either a polyether, polyester or polyurethane compound residue.

A subgeneric class of compounds included in the class of phosphoric or phosphonic acid ester compounds of formula (1), are compounds of the following formula (2).

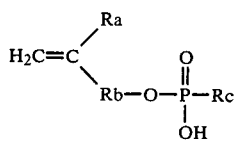

(2)

wherein Ra is hydrogen or methyl; Rb is COOY, OCOY, OY, Y, $CO(OCH_2CH_2)_m$, or

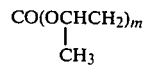

wherein m is an integer of 1 to 5, or

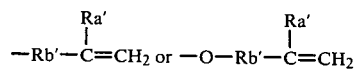

wherein l is an integer of 1 to 3, where Y is a straight-chain, cyclic or branched aliphatic, aromatic or alicyclic hydrocarbon residue containing 1 to 30 carbon atoms, which hydrocarbon residue may optionally be substituted by hydroxyl, alkoxy or halogen; Rc has the meaning defined hereinbefore. This particular subgeneric class of compounds includes compounds in which Rc is either

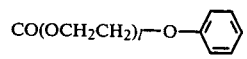

wherein Ra' and Rb' have the same meanings as Ra and Rb, respectively.

(B) The present compound may also be a compound of the following formula (3):

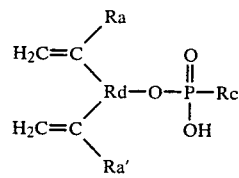

(3)

wherein Ra and Rc have the meanings defined hereinbefore; Ra' has the same meaning as Ra; Rd is

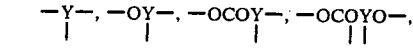

(1)

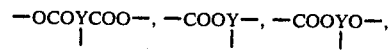

wherein Y has the meaning defined hereinbefore.

(C) The present compound may be a compound of one of the following formulas (4), (5) and (6).

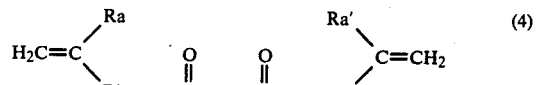

(4)

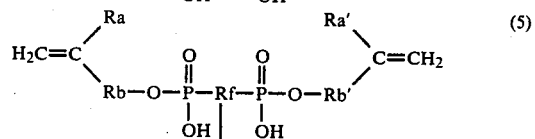

(5)

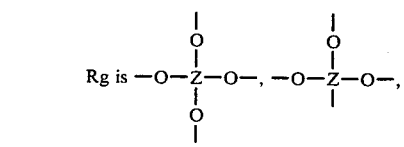

(6)

In the above formulas, Ra and Rb have the meanings hereinbefore defined; Ra', and Ra'' and Ra''' have the same meaning as Ra; Rb', Rb'' and Rb''' have the same meaning as Rb; Re is $-O-Z-O-$, $-O-Z-$ or $-Z-$;

Rf is $-O-Z-O-$, $-O-Z-O-$, $-O-Z-$ or $-Z-$;

Rg is $-O-Z-O-$, $-O-Z-O-$,

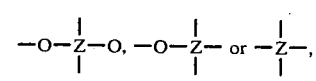

wherein Z has the same meaning as X.

(D) The present compound may be a compound of the following general formula (7):

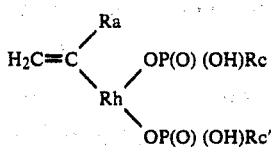

wherein Ra has the same meaning as hereinbefore defined; Rh is COOY, OCOY, OY or Y, wherein Y has the same meaning as hereinbefore defined; and Rc' has the same meaning as Rc which has been hereinbefore defined.

As will be apparent from the above description, the carbon atom of the P—C bond or P—O—C bond in the

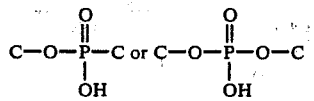

bond, as the case may be, may form a ring for the purposes of this invention.

The following is a partial list of the phosphoric or phosphonic acid ester compounds employed in the practice of this invention.

Compounds of formula (2) include:

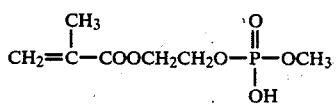

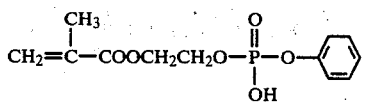

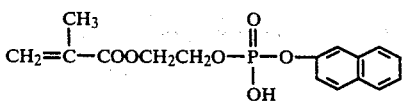

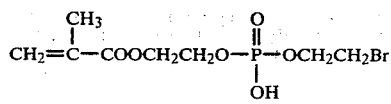

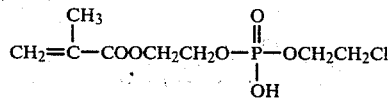

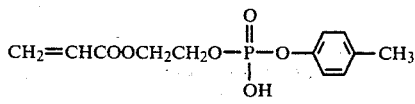

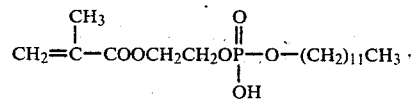

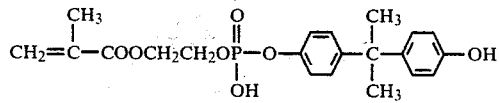

-continued

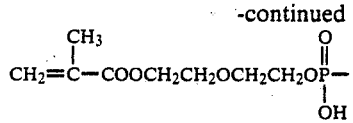

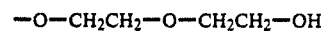

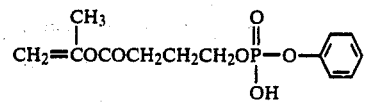

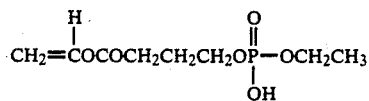

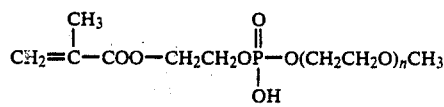

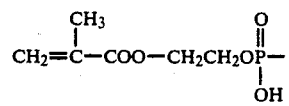

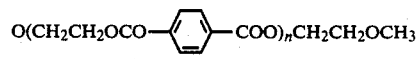

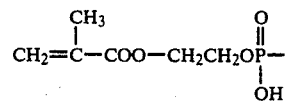

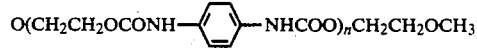

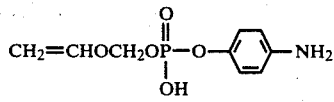

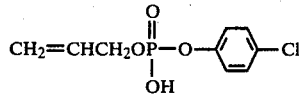

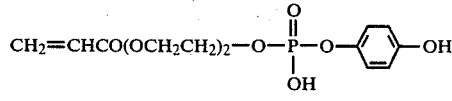

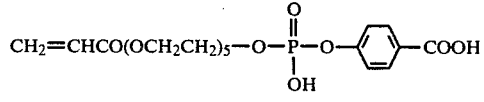

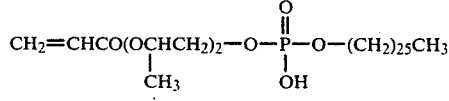

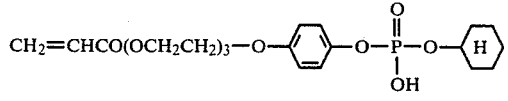

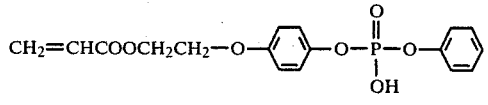

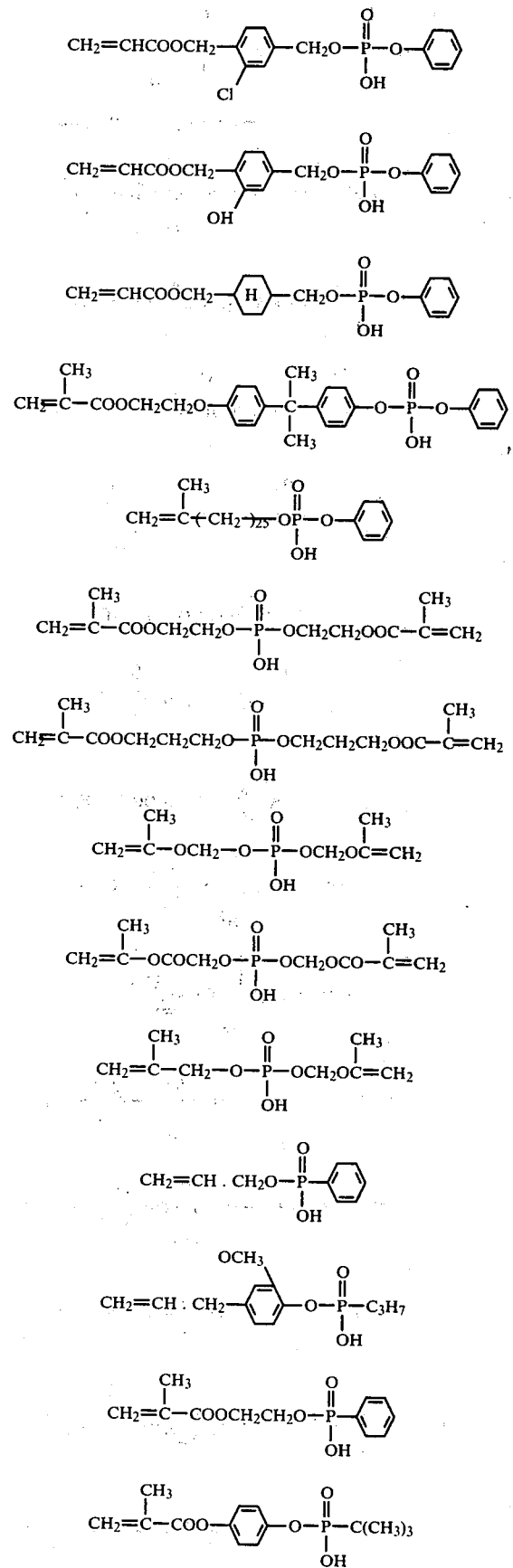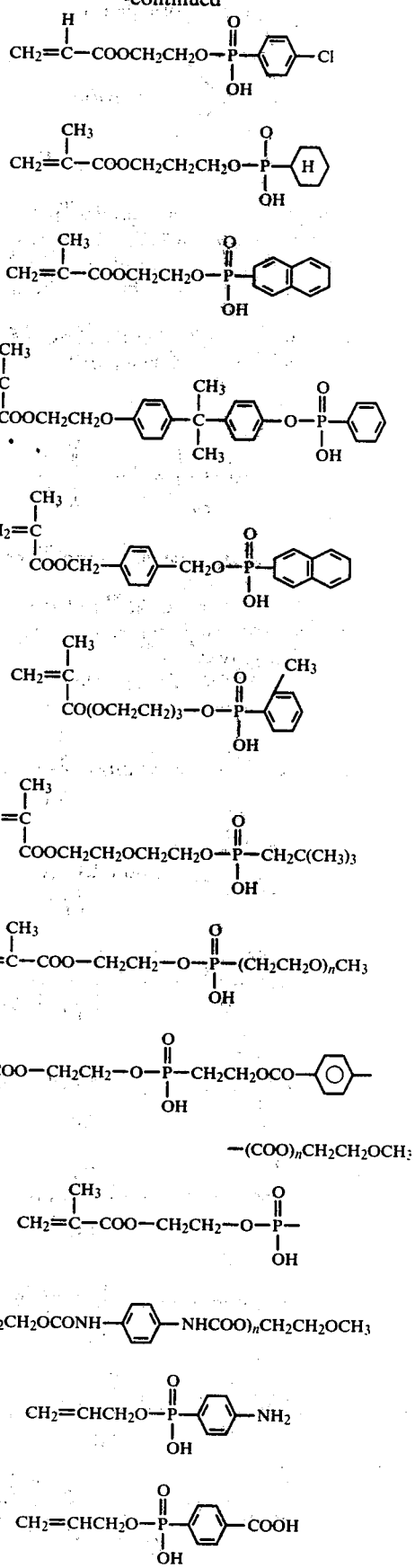

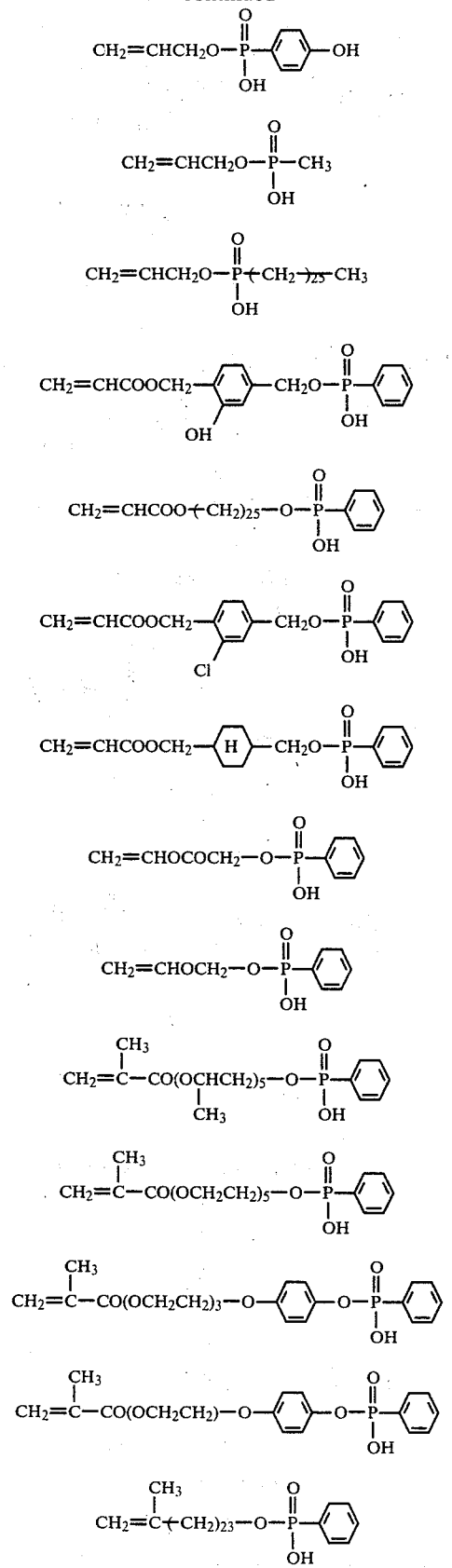
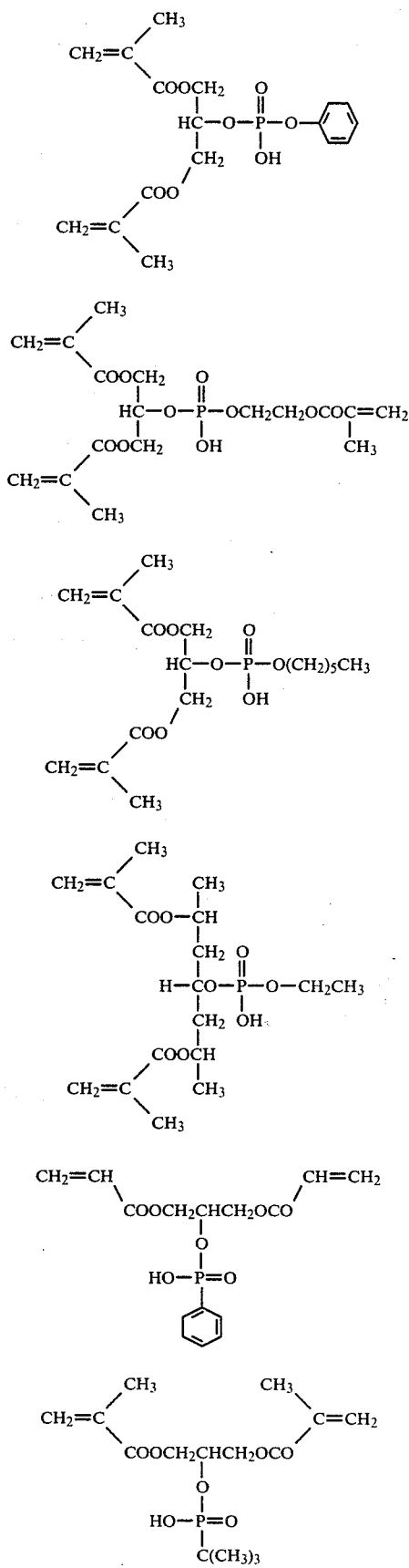
Compounds of formula (3) include:
Compounds of formula (4), (5) or (6) include:

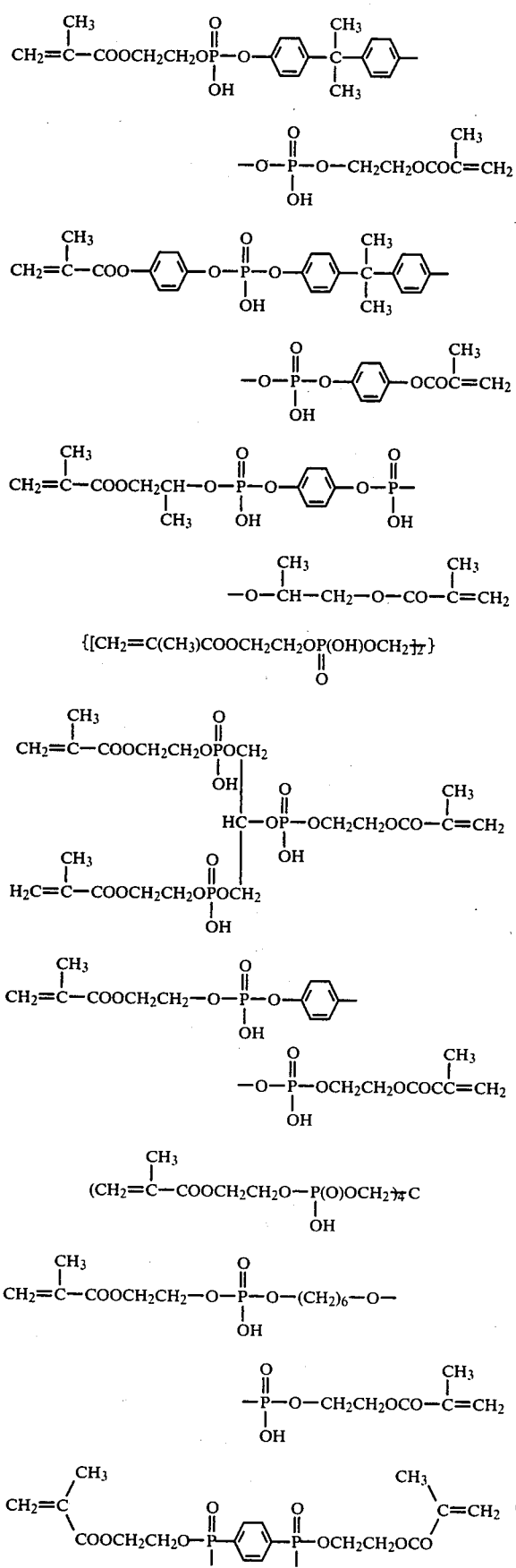
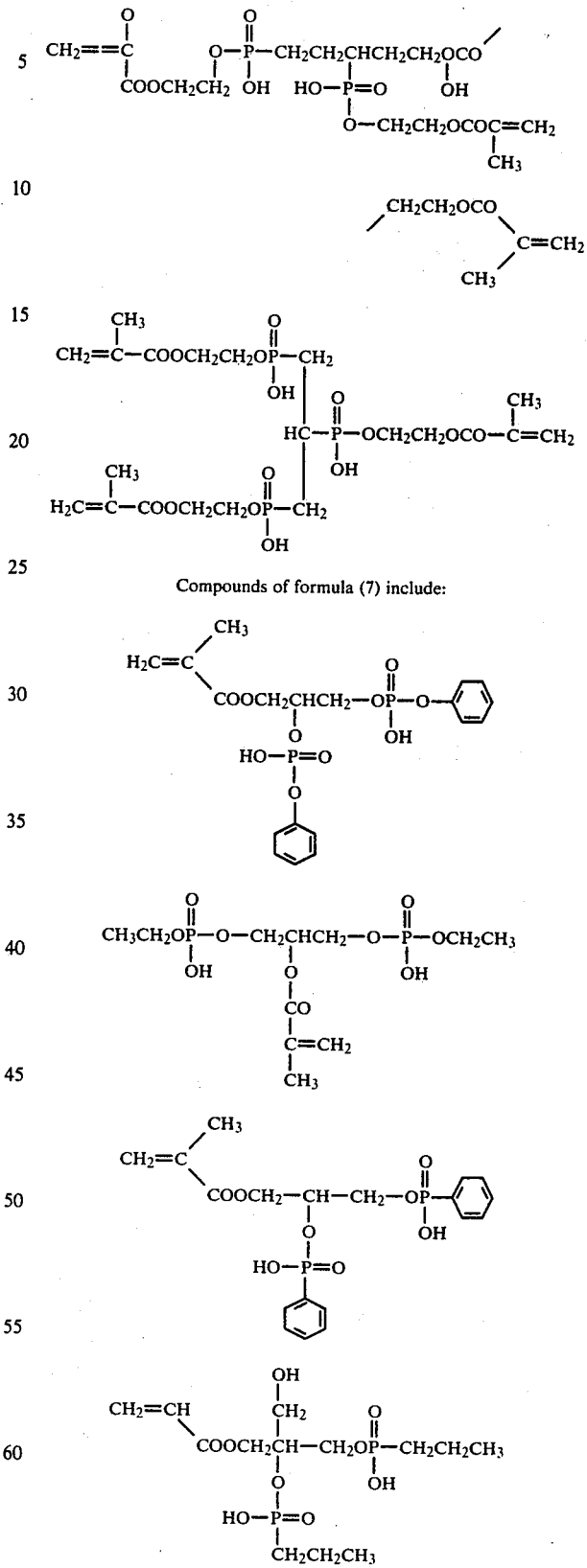
Compounds of formula (7) include:
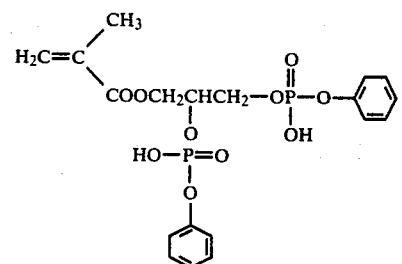
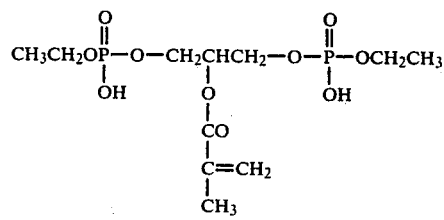
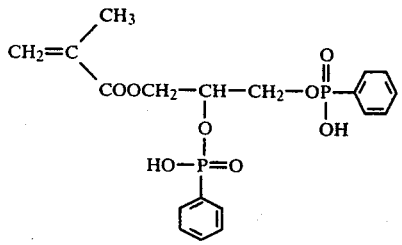
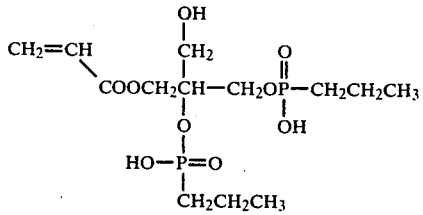
Further, the reaction product of phytic acid and glycidyl methacrylate of the following formula is also employed.

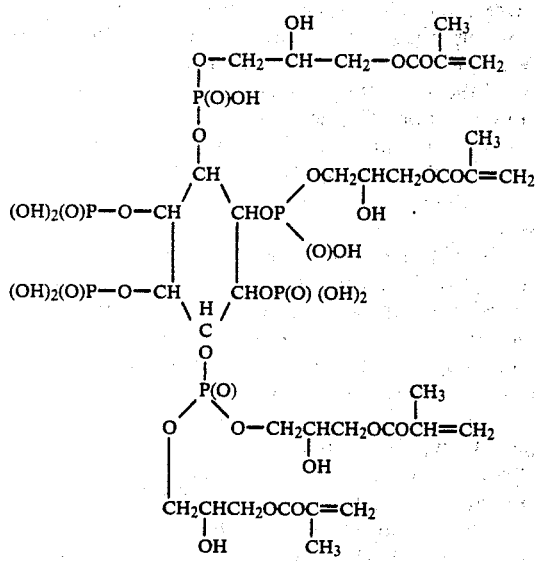

Among the foregoing compounds, the phosphonic acid ester compounds containing the

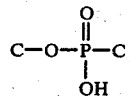

bond are more resistant to hydrolysis, are better conducive to sustained bonding strength under wet conditions and, therefore, are more desirable than the phosphoric acid ester compounds containing a

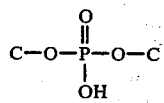

bond.

Furthermore, among the compounds of formula (2), those in which X is an alicyclic or aromatic hydrocarbon residue are superior to the compounds in which X is an aliphatic hydrocarbon residue with respect of bonding strength.

It may also be generally said that the phosphoric or phosphonic acid ester compounds containing two or more polymerizable functional groups, i.e. the compounds of formula (2), (4), (5) and (6), are more stable than the phosphoric or phosphonic acid ester compounds containing only one polymerizable functional group, because of the fact that even if one of the P—O—C bonds is hydrolyzed, the other P—O—C bond may remain intact and active.

These phosphoric or phosphonic acid ester compounds are preferably acid compounds from the standpoint of adhesive affinity for the hard tissue of the human body. However, to mitigate an irritating effect upon the tissue, the acid protons in such compounds may be partly, i.e. 10 to 90 mole %, used in the form of salts. Suitable salt forming elements or compounds include alkali metals, e.g. sodium and potassium the alkaline earth metals, e.g. magnesium and calcium; transition elements, ammonium, amines and so forth.

The compounds of formula (2) may normally be produced by the following reaction procedure, and the other compounds may also be produced by a similar procedure.

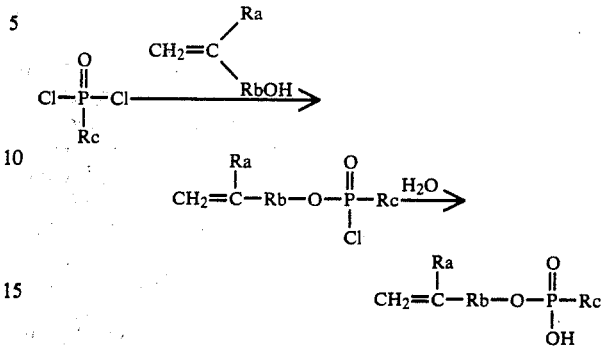

In the practice of this invention, the aforementioned phosphoric or phosphonic acid ester compound may be polymerized and cured at the time of application to the hard tissue of the human body or, alternatively, it may be previously polymerized and, after admixture with another monomeric component, be cured at the time of application to the tissue. As a further alternative, it may be previously polymerized and the resultant polymer may be dissolved or dispersed in a medium and applied to the hard tissue.

Among the aforementioned and other alternatives, the most convenient method in obtaining the strongest bond is the one which uses the aforementioned phosphoric or phosphonic acid ester compound in monomeric form and in which it is polymerized and cured in situ at the time of application to the hard tissue of the human body. In such cases, while the phosphoric or phosphonic acid ester compound may be polymerized alone, it is normally copolymerized with another monomer employable in cementing compositions for the hard tissue. Therefore, the term "polymer" in the context of this invention includes copolymers with other monomers. The polymerizable monomers which may thus be employed in conjunction with the present cement may be any polymerizable monomers having no injurious effects on human beings, such as methyl acrylate, ethyl acrylate, hydroxyethyl acrylate, ethylene glycol diacrylate, di-, tri- or tetraethylene glycol diacrylate, bisphenol A diacrylate, 2,2'-bis(acryloxyethoxyphenyl) propane, 2,2'-bis(γ-acryloxy-β-hydroxypropoxyphenyl)-propane, N,N-dimethylaminoethyl acrylate, glycidyl acrylate, and the all corresponding methacrylates, styrene, vinyl acetate, etc. It is also possible to employ monomers containing groups which are able to undergo low shrinkage ring-opening polymerization such as epoxy monomers, spiro-orthoesters, bicyclolactones, etc. There are cases in which, for the purpose of controlling the cure shrinkage, polymethyl methacrylate, polyethyl methacrylate, polystyrene, unsaturated polyester resins, high molecular epoxy acrylate resins, etc., are concomitantly employed.

Excellent bonding affinity for the hard tissue of the human body is realized when, in the composition, the aforementioned phosphoric or phosphonic acid ester compound and/or polymer of said compound is present in a proportion of no less than 0.1 weight percent or more, as phosphorus, of the form of

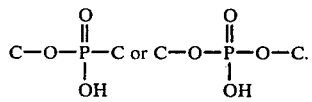

The curing agent which may be employed for the purposes of this invention is any agent that may effect the cure reaction at room temperature in a matter of a few minutes. For example, such systems as amine-peroxide, p-toluenesulfinic acid-peroxide, trialkylboron-peroxide and amine-salt of sulfinic acid-peroxide systems may be mentioned as well as ultraviolet sensitizers. In the above catalyst systems, the amine may for example be dimethyl-p-toluidine or N,N-diethanol-p-toluidine, and said peroxide may be for example, benzoyl peroxide, while the salt of sulfinic acid may be for example, sodium benzene sulfinate, sodium toluene sulfinate, sodium dodecyl benzene sulfinate, or ammonium toluene sulfinate. The ultraviolet sensitizer may be benzoin methyl ether, isopropoxybenzoin, p-benzoylbenzyl bromide, benzoin phenyl ether or benzoin isobutyl ether, for instance. The use of a curing system comprising a peroxide, amine and sulfinate is particularly desirable in that it provides a higher wet bond strength than does any other curing system so far known. If necessary, a polymerization inhibitor, e.g. hydroquinone monomethyl ether or 2,6-di-tert-butyl-p-cresol may also be incorporated in the cement composition as well as an antioxidant, ultraviolet absorber, pigment, etc. The adhesive cementing agent according to this invention is often used in such a manner that it is polymerized and caused to cure at the time of application to the hard tissue of the human body and, moreover, is expected to cure with rapidity in the neighborhood of room temperature or body temperature. Therefore, the adhesive cementing agent according to this invention must be prepared with consideration paid to the so-called pot life. As is customarily done with conventional cements for use on the hard tissue of the human body, there are some cases where the adhesive cementing agent of this invention is supplied to doctors or dentists in at least two separate packages, one of which contains the aforementioned phosphoric or phosphonic acid ester compound.

In such cases, the clinician admixes the contents of a package with the contents of another package or packages to produce a cured compound. In other cases the clinician irradiates the contents of a single package with ultraviolet or other rays to obtain a cured compound.

The adhesive cementing agent according to this invention, when used as compounded with a filling agent, may improve the bonding affinity of the cement for the hard tissue of the human body. Alternatively, the adhesive cementing agent may be coated onto the exposed surface of the tooth or bone and, then, the known cement or restorative applied, in which case the adhesion of the cement or restorative to the hard tissue is improved. The adhesive cementing agent of this invention may also be employed as an adhesive agent for inlays and crowns, because of its good affinity to metal. Therefore, the term "adhesive cementing agent" in the context of this invention includes dental adhesive agents for bonding dental filling material, inlays or crowns to the tooth, dental filler, dental restoratives, dental cements, bone cements for fixation of artificial joints, adhesive agents for the treatment of a complex fracture of bone, and so forth. The following description relates to the mode of embodiment of this invention in which, as a preferred use for the present adhesive cementing agent, it is employed as a cement for a dental filling composition or between the tooth and the filler. In such applications, the use of the phosphoric or phosphonic acid ester compound or polymer thereof according to this invention in admixture with the prior art cement results in a significantly improved bond with the hard tissue of the human body without resort to any modification in conventional procedure.

When the adhesive cementing agent of this invention is employed as a filling composition, the composition desirably comprises the aforementioned phosphoric or phosphonic acid ester compound, a polymerizable monomer, a filler material and a curing agent. Such a composition is polymerized after filling a cavity of the tooth and said phosphoric or phosphonic acid ester compound, on polymerization, displays an intimate bonding effect, providing a strong adhesion between the tooth and the filling composition without the use of any external adhesive agent. The composition preferably contains 2 to 50 weight percent, preferably 3 to 10 weight percent, of said phosphoric or phosphonic acid ester compound relative to said polymerizable monomer. No adequate bonding effect is achieved when the proportion is less, whereas a larger amount of the phosphoric or phosphonic acid ester compound tends to cause a depression in hardness. The polymerizable monomers which may be employed together with the aforementioned phosphoric or phosphonic acid ester compound are the monomers normally employed, example, bisphenol-A diglycidyl methacrylate as mentioned in U.S. Pat. No. 3,066,122, bisphenol-A dimethacrylate, 2,2-bis(4-methacryloxyethoxyphenyl) propane, 2,2-bis(4-methacryloxypropoxyphenyl)propane, xylylene glycol dimethacrylate, polyfunctional methacrylate esters, e.g. neopentyl glycol dimethacrylate, ethylene glycol dimethacrylate, triethylene glycol dimethacrylate, trimethylolpropane trimethacrylate, etc. and so forth. Normally these monomers are incorporated in a proportion of 10 to 50 weight percent based on the weight of the composition. The filler and curing agent may each be of the conventional variety. As the filler, silica powder, aluminum oxide powder and quartz powder silanated and having a particle diameter of 10 to 50μ are particularly desirable.

Where the adhesive agent according to this invention is employed as a cementing composition for bonding a dental filling material to the tooth, the adhesiive agent is applied as a priming layer between the tooth and filling composition. This application may be accomplished by any of the following techniques.

Thus, one of the following compositions is applied to the interface between the tooth and the dental filling composition, inlay or the like.

(1) A composition comprising an organic solvent having a boiling point not exceeding 80° C. and, as dissolved therein, the aforementioned phosphoric or phosphonic acid ester compound, the amount of which is not less than 5 weight %, preferably 5 to 20 weight %, based on the solution;

(2) A composition comprising a polymerizable monomer and, as incorporated therein, the aforementioned phosphoric or phosphonic acid ester compound, the amount of which is not less than 2 weight %, preferably 5 to 20 weight %, relative to said polymerizable monomer; or (3) A composition comprising a polymerizable monomer, a curing agent and, if necessary, a powdery vinyl polymer, and the aforementioned phosphoric or phosphonic acid ester compound, as incorporated in the monomer, the aforementioned phosphoric acid ester compound, the amount of which is not less than 2 weight %, preferably 3 to 15 weight %, based on the monomer, the proportion of the monomer being 30 to 99 weight percent of the composition.

The desired bonding effect is not attained when the ester compound is less than the aforementioned range in each instance, while an excess of the compound tends to detract from the water resistance of the composition.

The organic solvent employed in composition (1) is a low-boiling solvent substantially non-irritating to the dental pulp, such as ethanol, ethyl ether or chloroform. The polymerizable monomer employed in composition (2) is desirably based on a hydrophilic acrylic acid ester or methacrylic acid ester which has an affinity for the wet tooth. Preferred examples of such ester include hydroxyalkyl methacrylate such as 2-hydroxyethyl methacrylate and 3-hydroxypropyl methacrylate.

As to the monomer employed in composition (3), for the purposes of achieving improved hardness and water absorption characteristics, use is made of an aromatic methacrylate ester such as bisphenol A diglycidyl methacrylate and bisphenol A dimethacrylate as well as the forementioned polyfunctional methacrylate esters.

It will be apparent that the adhesive cementing agent according to this invention employs a compound containing polymerizable functional groups and monovalent phosphoric or phosphonic acid ester groups and, with an adhesive cementing agent, an intimate bond which has never been achieved by the prior art is obtained. It has further been established that this bond strength remains unaffected over a long time even under wet conditions, e.g. in the mouth or body. Furthermore, because clinically the cement composition of the present invention may be used by the conventional techniques without any substantial modification to obtain an intimate bond with the hard tissues of the human body, clinicians may employ the adhesive cementing agent of this invention with ease. It should also be in order to mention that, within the best knowledge of the present inventors, the phosphoric or phosphonic acid ester compound according to this invention has only negligible oral toxicity and no extraordinary injurious effects upon the pulp tissue.

The following examples are further illustrative but by no means limitative of this invention.

EXAMPLE 1

The resin compositions indicated below were tested for bond strength with wet dentin and enamel.

The crown of a fresh bovine tooth or a bar of fresh ivory was ground flat and finished with an emery paper #6/0 until the enamal or dentin was exposed. This bovine tooth or ivory bar was immersed in water for more than a day and, immediately before testing, the surface was wiped free of moisture. As to the bovine tooth, the enamal was etched with 50% phosphoric acid, washed with water and wiped free of moisture. The bovine tooth and ivory bar were coated with one of the test resin compositions. An acrylic resin bar was superimposed on the resin coat and the latter was allowed to cure. Thereafter, the assembly was held in water at 37° C. for 72 hours. The samples were then pulled apart to determine the bond strength. The average bond strength for 8 specimens is shown in Table 1.

A: A resin composition comprising a mixture of 50 weight parts of polymethyl methacrylate (mol. wt. 130,000), 40 weight parts of methyl methacrylate, 10 weight parts of ethylene glycol dimethacrylate, 2 weight parts of benzoyl peroxide, 4 weight parts of sodium p-toluenesulfinate and 2 weight parts of dimethyl-p-toluidine.

B∼N: A mixture of 100 weight parts of Resin Composition A and 10 weight parts of one of the following phosphoric or phosphonic acid ester compounds.

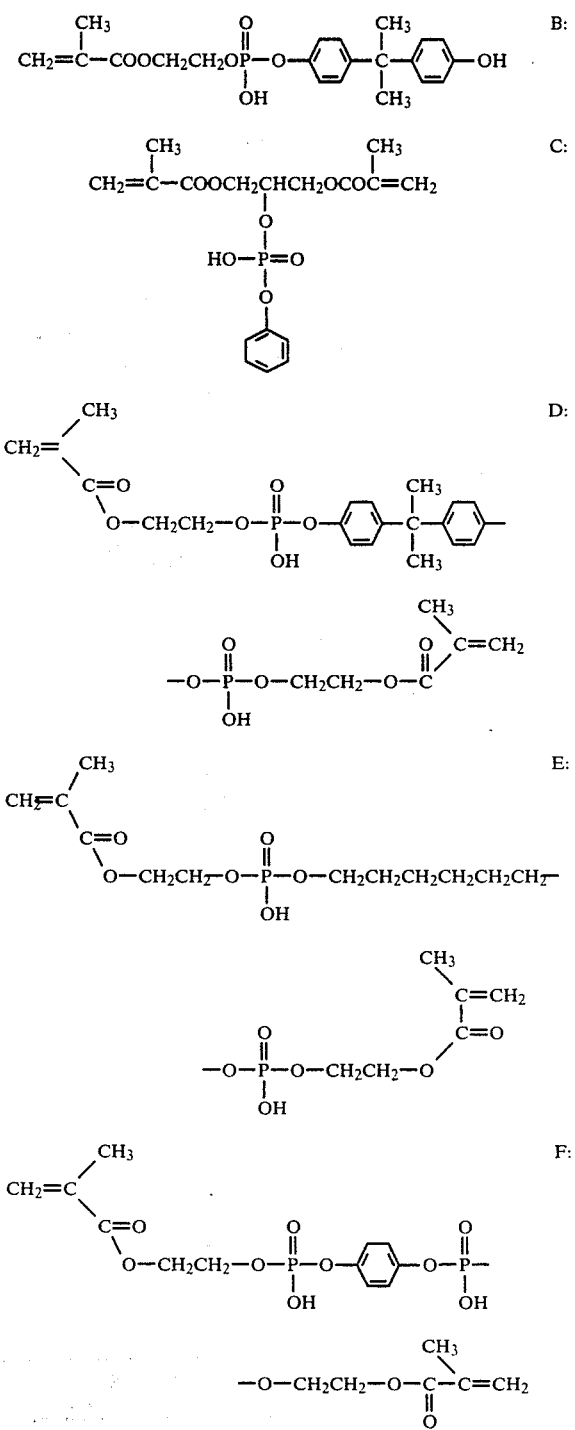

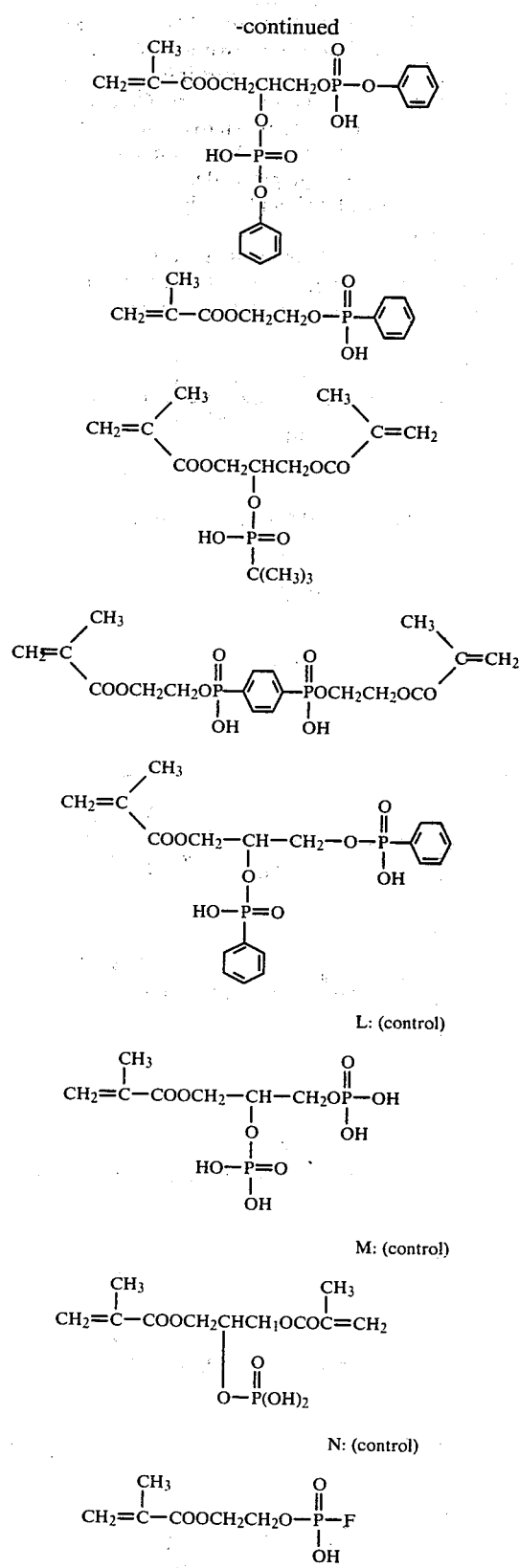

| | Bond strength (kg/cm$^2$) | |
|---|---|---|
| Resin composition | With dentin | With enamel |
| B | 121 | 107 |
| C | 160 | 109 |
| D | 151 | — |
| E | 138 | — |
| F | 146 | — |
| G | 154 | 96 |
| H | 170 | 115 |
| I | 90 | 112 |
| J | 163 | 110 |
| K | 187 | 89 |
| L | 21 | 114 |
| M | 25 | 92 |
| N | 79 | 104 |

It will be apparent from Table 1 that the adhesive cementing agents containing a phosphoric or phosphonic acid ester compound according to this invention (B-K) are superior to the adhesive cementing agent (A) which is free of the phosphoric or phosphonic acid ester compound in bonding affinity and that, in comparison to the phosphoric acid compounds (L-N) which are different from the phosphoric or phosphonic acid esters according to this invention in chemical structure, whereas there is no significant difference in bond strength with respect to the tooth enamel, the phosphoric or phosphonic acid ester cement according to this invention is by far superior in bond strength with respect to the dentin.

EXAMPLE 2

The following powder-liquid cementing systems containing the phosphoric acid ester compounds were prepared and, using ivory bars as in Example 1, these systems were tested for bonding affinities.

System A:

Two weight parts of benzoyl peroxide was added to 98 weight parts of polymethyl methacrylate powder, followed by thorough mixing to prepare a powdery material. To 95 weight parts of methyl methacrylate was added 5 weight parts of 2-methacryloxyethyl-phenyl acid phosphate (*1) together with 2.5 weight parts of p-toluenesulfinic acid to prepare a liquid component.

System B:

To 98 weight parts of polymethyl methacrylate powder was added 2 weight parts of benzoyl peroxide, followed by thorough mixing to prepare a powdery component. To 95 weight parts of methyl methacrylate were added 5 weight parts of 2-methacryloxyethyl 2-bromoethyl acid phosphate (*2) together with 2.5 weight parts of p-toluenesulfinic acid to prepare a liquid component.

The bond strengths found were 162 kg/cm$^2$ for System A and 90 kg/cm$^2$ for System B.

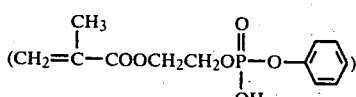

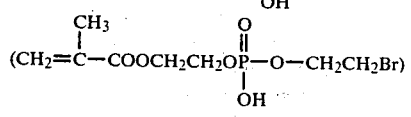

EXAMPLE 3

Coating compositions C and D were prepared by diluting the phosphoric acid ester monomer with a polymerizable monomer.

Composition C: This composition was prepared by diluting 10 weight parts of 2-methacryloxyethyl phenyl acid phosphate with 90 weight parts of 2-hydroxyethyl methacrylate.

Composition D: This composition was prepared by diluting 10 weight parts of 2-methacryloxyethyl 2-bromoethyl acid phosphate with 90 weight parts of 2-hydroxyoxyethyl methacrylate.

Separately, the following two kinds of filling pastes were prepared from a polymerizable monomer, an inorganic filler and a curing agent.

| P₁ Paste: | |
|---|---|
| Bisphenol A-diglycidyl methacrylate (hereafter referred to as Bis-GMA) | 16.8 weight parts |
| Triethylene glycol dimethacrylate | 2.8 weight parts |
| Silanated quartz powder | 80.1 weight parts |
| N,N-diethanol-p-toluidine | 0.3 weight parts |
| P₂ Paste: | |
| Bis-GMA | 16.8 weight parts |
| Triethylene glycol dimethacrylate | 2.8 weight parts |
| Silanated quartz powder | 80.0 weight parts |
| Benzoyl peroxide | 0.4 weight parts |

By means of a small brush, either Composition C or Composition D was sparingly applied to the end surface of an ivory bar. Then, the above two filling pastes were kneaded together for 30 seconds and superimposed on the coated primer. A bar of acrylic resin was then placed in abutment against the ivory bar end-to-end and the system was allowed to cure in situ to provide a bond between the bars. The bond strength was determined by the same procedure as hereinbefore described. The bond strength values were as high as 120 kg/cm² were Composition C was used as a primer coating, and 110 kg/cm² for Composition D. In a control run, where neither Composition C nor Composition D was employed, and no bond was established between the filling agent and dentin.

An extracted human molar was processed with an air turbine to produce a cavity about 4 mm in dia. and 3.5 mm deep in the neck portion of the tooth and the enamel of the tooth was etched with 50% aqueous phosphoric acid and rinsed well with water. Then, the cavity was dried with a current of air. After a thin coat of Composition C or Composition D was applied to the wall of the cavity, the above mixed filling paste was filled into the same cavity. The cure time was 4 minutes. The tooth was dipped in solutions of fuchsin at 0° C. and 60° C., in turn and 60 times each for a period of 1 minute per dipping. The marginal sealing effect was investigated in terms of dye penetration. The test showed no evidence of dye penetration.

EXAMPLE 4

14.5 Weight parts of Bis-GMA, 3.0 weight parts of neopentyl glycol dimethacrylate, 1.8 weight parts of 2-methacryloxyethyl phenyl acid phosphate, 80.7 weight parts of the same silanated quartz powder as that used in Example 3 and 0.5 weight parts of benzoyl peroxide were kneaded into a paste and, immediately before use, p-toluenesulfinic acid was added in a proportion of 1.0 weight part based on the total weight. This filling composition cured in about 5 minutes.

By the same procedure as described Example 3, the above filling composition was filled into the an extracted molar and examined for a marginal sealing effect around the cavity. No ingress of the dye was observed, attesting to the excellent sealing effect of the composition. In contrast, with a filling composition free from the phosphoric acid ester compound as used under the same conditions as above, the penetration of dye in many instances reached the bottom of the cavity, providing only poor sealing effects.

EXAMPLE 5

The following components E and F were prepared as a cold-cure powder-liquid resin system.

Component E:
95 Weight parts of polymethyl methacrylate (mol. wt. 250,000) were mixed with 3 weight parts of sodium p-toluenesulfinate and 2 weight parts of dibenzoyl peroxide to prepare a powdery component.

Component F:
80 Weight parts of methyl methacrylate were mixed with 10 weight parts of ethylene glycol dimethacrylate, 9 weight parts of bis-(2-methacryloxyethyl) acid phosphate (*1) and 1 weight part of N,N'-diethanol-p-toluidine to prepare a liquid component.

Equal weight parts of components E and F were placed in a glass vessel and stirred together for 1 minute. The resultant mixture was coated onto the end face of a bar of ivory and of an acrylic resin bar and the two end faces were butted against each other. The bond strength achieved between the bars as determined by the procedure described hereinbefore is shown in Table 2. A stable, high bond strength was evident even after prolonged immersion in water.

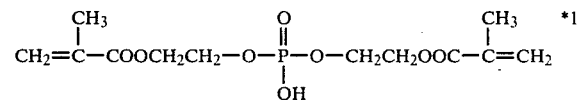

*1

TABLE 2

| No. of days of immersion in water at 37° C. | 1 day | 7 days | 30 days | 90 days |
|---|---|---|---|---|
| Average bond strength (kg/cm²) | 150 ± 45 | 173 ± 47 | 138 ± 50 | 165 ± 65 |

EXAMPLE 6

40 Weight parts of diethylene glycol dimethacrylate were mixed well with 60 weight parts of bisphenol-A diglycidyl methacrylate and 330 weight parts of silanated α-quartz powder (particle diam. 10~50μ) and the mixture was divided into two equal parts. To one of the halves was added 10 weight parts of the compound of formula:

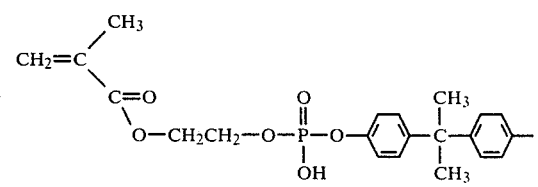

-continued

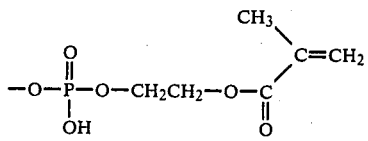

together with 2 weight parts of benzoyl peroxide. To the other half was added 2 weight parts of N,N-dimethyl-p-toluidine together with 2 weight parts of sodium p-toluenesulfinate. Before use, equal portions of the two pastes were thoroughly kneaded together, applied between bars of ivory and allowed to cure in situ. The mixed paste started curing about 3 minutes after the start of admixing and set sufficiently in about 10 minutes. The joined bar of ivory was maintained in water at 37° C. for 3 days, after which the bond strength was determined on an Instron ® tensile tester. While there was some variation between specimens, the range of bond strengths for ten bars was 108 to 190 kg/cm², the average being 178 kg/cm².

Portions of the above two pastes were admixed and placed into a #1 cavity formed in an extracted tooth, after phosphoric acid etching. The specimens were subjected to a percolation test which comprised dipping them into aqueous dye baths at 4° and 60° C., in turn and for a total of 100 times each, one minute per dipping. Substantially none of the specimens tested betrayed a penetration of the dye into the dentin, thus attesting to the satisfactory and improved bond between the tooth and filling agent.

EXAMPLE 7

20 Weight parts of the same phosphoric acid ester compound as used in Example 6 were mixed with a viscous fluid consisting of 30 weight parts of tetraethylene glycol dimethacrylate, 10 weight parts of hydroxyethyl methacrylate, 60 weight parts of methyl methacrylate and 20 weight parts of polymethyl methacrylate (mol. wt. 130,000). The resultant liquid composition was used to coat the etched (phosphoric acid) walls of the cavities in extracted teeth, which cavities had been formed by the removal of the decayed portion of the dentin, and had no retention form. Then, the cavities were filled with a commercial composite resin (Johnson & Johnson; Adaptic ®). These tooth specimens were subjected to a percolation test similar to that described in Example 6. The results indicated quite satisfactory marginal sealing effects.

EXAMPLE 8

10 Weight parts of the same phosphoric acid ester compound as that used in Example 6 was incorporated in a viscous fluid consisting of 10 weight parts of tetraethylene glycol dimethacrylate, 90 weight parts of methyl methacrylate and 20 weight parts of polymethyl methacrylate (mol. wt. 130,000).

To this fluid was added 1 weight % of benzoyl peroxide together with 1 weight % of dimethyl-p-toluidine and 3 weight % of sodium p-toluenesulfinate. The mixture was coated onto the surface of a tooth and a polycarbonate orthodontial bracket was fitted over the coated tooth. The bond between the tooth and bracket was quite satisfactory and remained stable over a long time.

EXAMPLE 9

As powder-liquid cementing systems, compositions G and H were prepared using different phosphonic acid monomers.

System G:

To 100 weight parts of polymethyl methacrylate powder was added 2 weight parts of benzoyl peroxide together with 3 weight parts of sodium p-toluenesulfinate and the mixture was stirred well to prepare a powdery component. To a mixture of 80 weight parts of methyl methacrylate and 10 weight parts of ethylene glycol dimethacrylate was added 10 weight parts of 2-methacryloxyethyl phenyl phosphonic acid (*1) together with 1.0 weight parts of N,N'-diethanol-p-toluidine to prepare a liquid component.

System H:

To 100 weight parts of polymethyl methacrylate powder was added 2 weight parts of benzoyl peroxide together with 3 weight parts of sodium p-toluenesulfinate and the mixture was blended well to prepare a powdery component. To a mixture of 80 weight parts of methyl methacrylate and 10 weight parts of ethylene glycol dimethacrylate was added 10 weight parts of 2-methacryloxyethyl isobutyl-phosphonic acid (*2) together with 1.0 weight part of N,N'-diethanol-p-toluidine to prepare a liquid component. Equal portions (by weight) of the powder and fluid of the above system G or H were kneaded together and the mixture was used to coat the end face of a rectangular bar of ivory to provide a relatively thick coat. A rectangular acrylic resin bar with a cross sectional area of 10×10 mm was butted against the above coated face and the system was allowed to cure in situ.

The joined bar was immersed in water at 37° C. for 48 hours, after which the bond strength was determined using an autograph.

In the case of System G, the average bond strength was 160 kg/cm², while System H provided an average bond strength of 148 kg/cm². These values are considerably higher than the average value of 35 kg/cm² for the corresponding systems G and H free of the phosphonic acid ester compound.

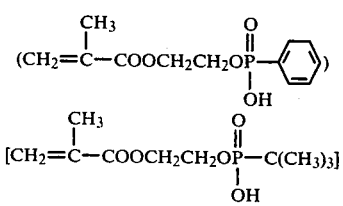

EXAMPLE 10

The following system containing the phosphonic acid ester compound of this invention was prepared.

| Component I: | |
|---|---|
| Bisphenol A-diglycidyl dimethacrylate | 14.3 weight parts |
| 2-Methacryloxyethyl phenyl phosphonic acid | 4.4 weight parts |
| Triethylene glycol dimethacrylate | 3.3 weight parts |
| Silanated α-quartz powder | 77.5 weight parts |
| Benzoyl peroxide | 0.45 weight part |
| Hydroquinone monomethyl ether | 0.05 weight part |
| Component J: | |
| Bisphenol A-diglycidyl dimethacrylate | 18.7 weight parts |
| Triethylene glycol dimethacrylate | 3.3 weight parts |
| Silanated α-quartz powder | 77.2 weight parts |

| | |
|---|---|
| Sodium p-toluenesulfinate | 0.55 weight part |
| N,N'-diethanol-p-toluidine | 0.2 weight part |
| Hydroquinone monomethyl ether | 0.05 weight part |

Equal portions, by weight, of Component I and Component J were taken and thoroughly kneaded together. The resultant system cured in 3 minutes.

The bond strength provided by the kneaded paste with respect to a bar of ivory was determined. The bond strength after 24 hours' immersion in water was 95 kg/cm². An extracted healthy human front tooth was processed with an air turbine in the routine manner to form a cavity 3 mm in diameter and 2 mm deep and, then, the enamel was etched with 50% aqueous phosphoric acid, rinsed with water and dried with a current of air. The equal weight portions of component I and component J were kneaded and the cavity was filled with the obtained paste. The tooth specimen was dipped in aqueous solutions of fuchsin at 0° C. and 60° C., in turn and for a total of 60 times, one minute per dipping. This percolation test showed substantially no evidence of dye penetration.

EXAMPLE 11

10 Weight parts of 2-methacryloxyethyl phenyl phosphonic acid was mixed with a fluid consisting of 30 weight parts of tetraethylene glycol dimethacrylate, 40 weight parts of 2-hydroxyethyl methacrylate and 20 weight parts of methyl methacrylate.

To this fluid was added 3 weight % of sodium p-toluenesulfinate and, after thorough mixing, the mixture was applied to the end faces of wet bars of ivory with a small brush to provide a thin coat. Then, equal parts of the two pastes of the commercial composition Adaptic ® (trade name, Johnson & Johnson) were mixed well and inserted and allowed to cure between the bars of ivory. The above procedure provided an intimate bond. The joined bar was maintained in water at 37° C. for 1 to 30 days and the bond strength values were determined. The results are set forth in Table 3.

TABLE 3.

| No. of days of immersion in water | 1 | 14 | 30 |
|---|---|---|---|
| Bond strength (kg/cm²) | 155 | 142 | 151 |

Using an extracted healthy human front tooth, the above composition was used to coat the cavity in the same manner as above and the tooth was subjected to a percolation test similar to that described in Example 6. The result was an excellent marginal seal.

EXAMPLE 12

The surface of an extracted healthy tooth was treated with a 50% aqueous solution of phosphoric acid and rinsed well with water. 10 Weight parts of (2-methacryloxyethyl)-β-naphthylphosphonic acid (*1) were mixed with 10 weight parts of tetraethylene glycol dimethacrylate, 80 weight parts of methyl methacrylate and 30 weight parts of polymethyl methacrylate (mol. wt. 130,000).

To this fluid was added 1 weight % of benzoyl peroxide together with 1 weight % of dimethyl-p-toluidine and 3% of sodium p-toluenesulfinate and, after thorough mixing, the mixture was coated onto the surface of the above tooth. Then, a polycarbonate orthodontial bracket was fitted over the coated tooth. An excellent bond between the tooth and bracket was obtained with the bond strength being stable over a long period.

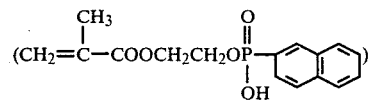

EXAMPLE 13

A three-necked flask of 300 ml capacity, fitted with a stirrer, condenser and thermometer, was charged with 200 g of toluene, 40 g of methyl methacrylate, 2 g of (2-methacryloxyethyl) phenylphosphonic acid (*1) and 0.2 g of benzoyl peroxide.

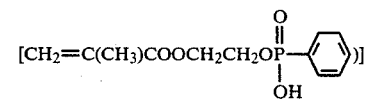

Under vigorous stirring, the polymerization reaction was continued at 90° C. for 3 hours. After cooling, the reaction mixture was added to a large quantity of ethyl ether to reprecipitate the polymer. The polymer was dried well and comminuted to prepare a microfine powder not larger than 200 mesh.

To 100 weight parts of this finely divided polymer was added 3 weight parts of sodium p-toluenesulfinate together with 2 weight parts of benzoyl peroxide, followed by thorough mixing to prepare a powdery component.

To a mixture of 80 weight parts of methyl methacrylate and 20 weight parts of ethylene glycol dimethacrylate was added 1 weight part of N,N'-diethanol-p-toluidine. The resultant monomeric composition and the above powdery component were used to coat the end face of a rectangular bar of ivory with a brush to provide a comparatively thick coat and the end face of a rectangular bar of acrylic resin was placed in abuttment against the above coated end face.

The joined bar was immersed in water at 37° C. for 24 hours and, then, the bond strength was determined using an Autograph ®. The average bond strength for 10 specimens was as high as 154 kg/cm².

A composition was prepared by the same procedure as above except that (2-methacryloxyethyl) phenyl phosphoric acid

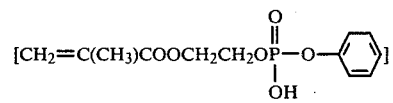

was used in lieu of said (2-methacryloxyethyl)phosphonic acid and the bond strength was determined under the same conditions as above. The average bond strength was 162 kg/cm².

EXAMPLE 14

The following components were prepared for a two liquid cementing system for liner use and a two paste composite resin system.

| Component K (liquid) | |
|---|---|
| 2-Methacryloxyethyl phenyl acid phosphate | 20 weight parts |

-continued

| | |
|---|---|
| Bisphenol A-diglycidyl methacrylate | 10 weight parts |
| Neopentyl glycol dimethacrylate | 60 weight parts |
| Methacrylic acid | 10 weight parts |
| Benzoyl peroxide | 3 weight parts |
| Hydroquinone monomethyl ether | 0.05 weight part |
| Component L (liquid) | |
| 2 Hydroxyethyl methacrylate | 40 weight parts |
| Bisphenol A-diglycidyl methacrylate | 40 weight parts |
| Diethylene glycol dimethacrylate | 20 weight parts |
| Sodium benzene sulfinate | 2 weight parts |
| N,N-diethanol-p-toluidine | 3 weight parts |
| Hydroquinone monomethyl ether | 0.05 weight part |
| Component M | |
| The same paste as $P_1$ used in Example 3. | |
| Component N | |
| The same paste as $P_2$ used in Example 3. | |

In an extracted tooth a cavity about 2 mm in dia. and 4 mm deep was formed. The cavity and the enamel part around the cavity were coated with a paste comprising a 50% phosphoric acid aqueous solution and 10 wt % Aerosil ® to the said solution, then rinsed with water after 1 minute and dried with a current of air. Equal weight portions of component K and component L were mixed and coated on the wall of the cavity and the enamel part around the cavity. The equal weight portions of component M and component N were kneaded together and the cavity was filled. After a lapse of 5 minutes, the filled cavity was polished with a diamond tool and then with a paste-like finishing agent. The tooth was, from the aesthetical and mechanical view point, perfectly repaired with this treatment. A quite satisfactory marginal sealing effect was observed.

We claim as our invention:

1. A dental filling material of improved affinity for the tooth, consisting essentially of:
   (1) an acrylic or methacrylic acid ester compound,
   (2) a curing agent and (3) a dentally acceptable filler as a mixed material in combination with a phosphoric and/or phosphonic acid ester compound selected from the group consisting of compounds of formulas (A), (B), (C), (D), (E) and (F) in an amount of 2 to 50 weight percent based on said acrylic or methacrylic acid ester compound, said formulas being:

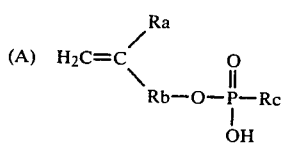

(A)

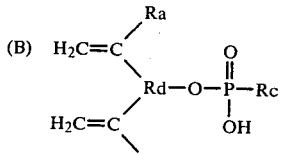

(B)

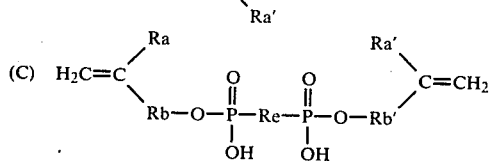

(C)

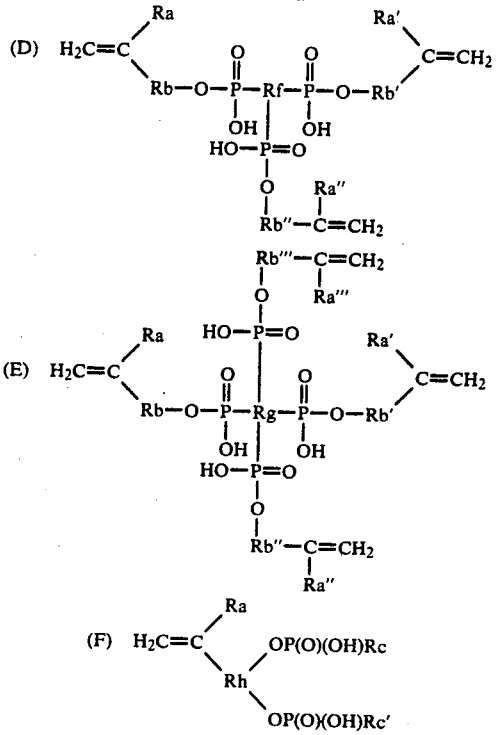

(D)

(E)

(F)

wherein Ra, Ra', Ra" and Ra'" are hydrogen or methyl; Rb, Rb', Rb" and Rb'" are $$COOY, OCOY, OY, Y, CO(OCH_2CH_2)_m, CO(OCHCH_2)_m$$
$$\phantom{COOY, OCOY, OY, Y, CO(OCH_2CH_2)_m, CO(OCHCH_2)} CH_3$$

wherein m is an integer of 1 to 5 or

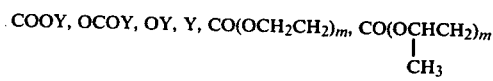

wherein l is an integer of 1 to 3; Y is a hydrocarbon residue containing 1 to 30 carbon atoms, which residue may be substituted by hydroxyl, alkoxy or halogen; Rc and Rc' are X or OX where X is a hydrocarbon residue containing 1 to 30 carbon atoms, which may be substituted by hydroxyl, halogen, amino or carboxyl;

$$Rd \text{ is } -Y-, -OY-, -OYO-, -OCOY-, -OCOYO-,$$
$$-OCOYCOO-, -COOY-, -COOYO-, -COOYCOO-$$
$$\text{or } -COOYOCO-;$$

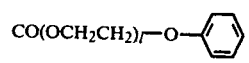

$Rf$ is $-O-Z-O-$, $-O-Z-$, $-O-Z-$ or $-Z-$;
$\phantom{Rf \text{ is } -O-Z-O-, -O-Z-,} O \phantom{-O-Z-} O$
$\phantom{Rf \text{ is } -O-Z-O-, -O-Z-,} | \phantom{-O-Z-} |$ $Rg$ is $-O-Z-O-$, $-O-Z-O-$,
$\phantom{Rg \text{ is }} O \phantom{-O-Z} O$
$\phantom{Rg \text{ is }} | \phantom{-O-Z} |$ -continued

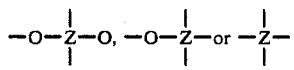

where Z has the same meaning as X, and

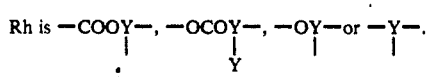

2. The dental filing material of claim 1, wherein said phosphoric or phosphonic acid ester compound is a compound having formula (G) or (H):

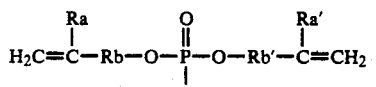

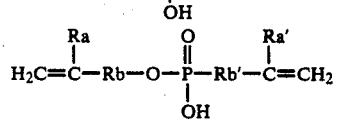

wherein Ra, Ra', Rb and Rb' are as defined in claim 1.

3. The dental filling material of claim 1, wherein said phosphoric acid ester compound is 2-methacryloxyethyl phenyl phosphoric acid.

4. The dental filling material of claim 1, wherein said phosphonic acid ester compound is 2-methacryloxyethyl phenyl phosphonic acid.

5. The dental filling material of claim 2, wherein said phosphoric acid ester compound is bis-(2-methacryloxyethyl) acid phosphate.

6. The dental filling material of claim 1, 2, 3, 4 or 5, wherein said acrylic or methacrylic acid ester compound is present in an amount of 10 to 50 weight % based on said mixed material.

7. The dental filling material of claim 6, wherein said methacrylic acid ester compound is selected from the group consisting of bisphenol-A diglycidyl methacrylate, bisphenol-A dimethacrylate, 2,2'-bis(4-methacryloxyethoxyphenyl) propane, 2,2'-bis(4-methacryloxypropoxyphenyl) propane, xylene glycol dimethacrylate, neopentyl glycol dimethacrylate, ethylene glycol dimethacrylate, diethylene glycol dimethacrylate, triethylene glycol dimethacrylate, and trimethylolpropane trimethacrylate.

8. The dental filling material of claim 1, 2, 3, 4 or 5, wherein said curing agent is one which cures at room temperature.

9. The dental filling material of claim 1, 2, 3, 4, or 5, wherein said curing agent is an ultraviolet sensitizer.

10. The dental filling material of claim 1, 2, 3, 4 or 5, wherein said filler is selected from the group consisting of silica powder, aluminum oxide powder and quartz powder which are silinated.

* * * * *

UNITED STATES PATENT AND TRADEMARK OFFICE
CERTIFICATE OF CORRECTION

PATENT NO. : 4,259,117

DATED : March 31, 1981

INVENTOR(S) : JUNICHI YAMAUCHI ET AL

It is certified that error appears in the above-identified patent and that said Letters Patent are hereby corrected as shown below:

Column 4, lines 1-10: delete existing formula and insert therefor:

$$-Y-, \quad -OY-, \quad -OYO-, \quad -OCOY-, \quad -OCOYO-,$$

$$-OCOYCOO-, \quad -COOY-, \quad -COOYO-,$$

$$-COOYCOO- \text{ or } -COOYOCO-,$$

Column 4, lines 51-55: delete existing formula and insert therefor:

$$-O-Z-O-, \quad -O-Z- \text{ or } -Z-;$$

Rf is $-O-Z-O-, \quad -O-Z-, \quad -O-Z-$ or $-Z-;$

UNITED STATES PATENT AND TRADEMARK OFFICE
CERTIFICATE OF CORRECTION

PATENT NO. : 4,259,117
DATED : MARCH 31, 1981
INVENTOR(S) : JUNICHI YAMAUCHI ET AL

It is certified that error appears in the above-identified patent and that said Letters Patent are hereby corrected as shown below:

Column 8, lines 7-10: delete existing formula and insert therefor:

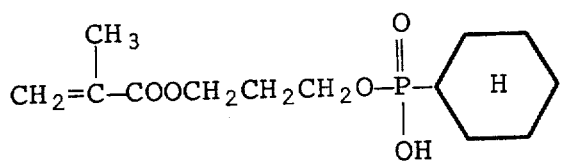

Column 8, lines 34-39: delete existing formula and insert therefor:

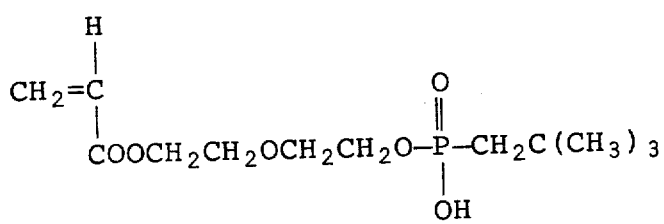

Column 8, lines 45-50: delete existing formula and insert therefor:

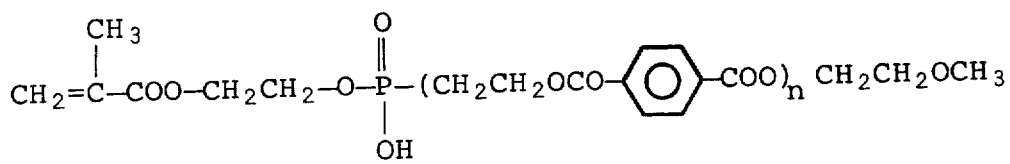

UNITED STATES PATENT AND TRADEMARK OFFICE
CERTIFICATE OF CORRECTION

PATENT NO. : 4,259,117
DATED : March 31, 1981
INVENTOR(S) : JUNICHI YAMAUCHI ET AL It is certified that error appears in the above-identified patent and that said Letters Patent are hereby corrected as shown below:

Column 11, lines 46-50: delete existing formula and insert therefor:

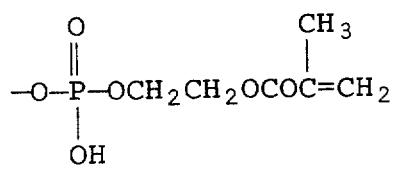

Column 12, lines 3-9: delete existing formula and insert therefor:

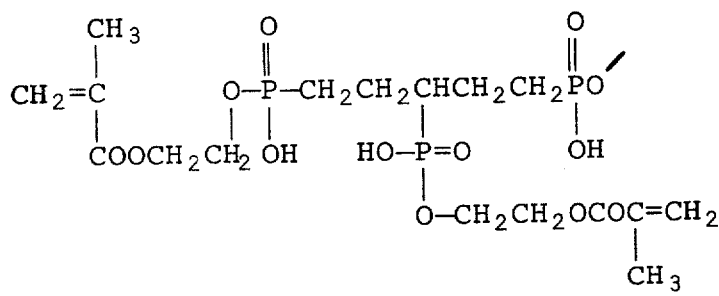

UNITED STATES PATENT AND TRADEMARK OFFICE
CERTIFICATE OF CORRECTION

PATENT NO. : 4,259,117
DATED : MARCH 31, 1981
INVENTOR(S) : JUNICHI YAMAUCHI ET AL

It is certified that error appears in the above-identified patent and that said Letters Patent are hereby corrected as shown below:

Column 18, lines 28-35: delete existing formula and insert therefor:

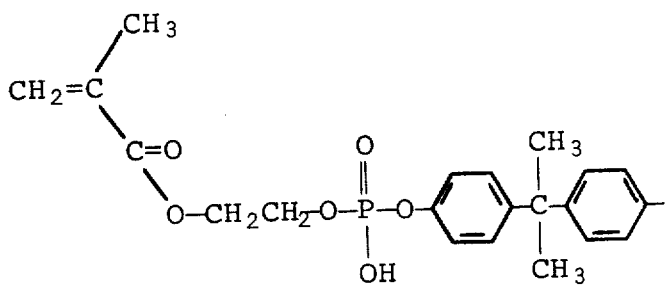

Column 19, lines 51-56: delete existing formula and insert therefor:

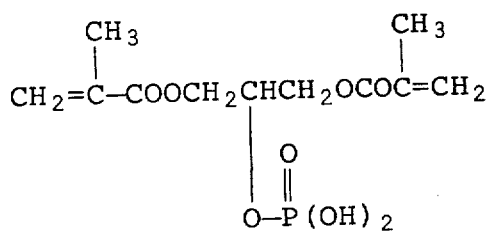

UNITED STATES PATENT AND TRADEMARK OFFICE
CERTIFICATE OF CORRECTION

PATENT NO. : 4,259,117
DATED : March 31, 1981
INVENTOR(S) : Junichi Yamauchi et al It is certified that error appears in the above—identified patent and that said Letters Patent is hereby corrected as shown below:

Column 21, line 39: delete "were" and insert therefor

--where--

Column 26, lines 17-21: delete existing formula and insert therefor:

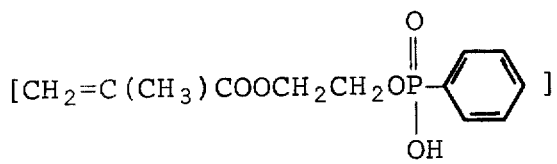

UNITED STATES PATENT AND TRADEMARK OFFICE
CERTIFICATE OF CORRECTION

PATENT NO. : 4,259,117

DATED : March 31, 1981

INVENTOR(S) : Junichi Yamauchi et al

It is certified that error appears in the above—identified patent and that said Letters Patent is hereby corrected as shown below:

Column 28, line 44: delete "1" and insert --$\ell$-- as follows:

wherein $\ell$ is an integer of 1 to 3; Y is a hydrocarbon

Column 29, lines 10-12: delete existing formula and insert therefor:

$$Rh \text{ is } -\underset{|}{C}OOY-, -\underset{|}{O}COY-, -\underset{|}{O}Y- \text{ or } -\underset{|}{Y}-.$$

Signed and Sealed this

Nineteenth Day of January 1982

[SEAL]

Attest:

*Attesting Officer*

GERALD J. MOSSINGHOFF

*Commissioner of Patents and Trademarks*